US009732714B2

United States Patent
Anderson et al.

(10) Patent No.: US 9,732,714 B2
(45) Date of Patent: Aug. 15, 2017

(54) METHOD AND SYSTEM FOR WATER DRAINAGE IN FUEL SYSTEM

(71) Applicant: General Electric Company, Schenectady, NY (US)

(72) Inventors: Larry Gene Anderson, Erie, PA (US); Sivanaga Venu Varma Dantuluri, Folsom, CA (US); Dennis Shea, Grove City, OH (US); Morse N. Taxon, Erie, PA (US)

(73) Assignee: General Electric Company, Schenectady, NY (US)

( * ) Notice: Subject to any disclaimer, the term of this patent is extended or adjusted under 35 U.S.C. 154(b) by 566 days.

(21) Appl. No.: 14/186,718

(22) Filed: Feb. 21, 2014

(65) Prior Publication Data

US 2014/0166596 A1    Jun. 19, 2014

Related U.S. Application Data

(63) Continuation-in-part of application No. 12/859,879, filed on Aug. 20, 2010, now abandoned.

(51) Int. Cl.
*B01D 21/24* (2006.01)
*G05D 1/00* (2006.01)
(Continued)

(52) U.S. Cl.
CPC ....... *F02M 37/221* (2013.01); *F02D 19/0605* (2013.01); *F02M 35/042* (2013.01); *G01N 33/2847* (2013.01)

(58) Field of Classification Search
None
See application file for complete search history.

(56) References Cited

U.S. PATENT DOCUMENTS 3,249,229 A * 5/1966 Kasten ................... B60K 15/00
210/195.1
4,015,237 A  3/1977 Takatani et al.
(Continued)

FOREIGN PATENT DOCUMENTS

DE  4409570 A1  5/1995
EP  0671631 A2  9/1995
(Continued)

OTHER PUBLICATIONS

ISA European Patent Office, International Search Report and Written Opinion of PCT/US2011/039555, Feb. 1, 2012, WIPO, 13 pages.

*Primary Examiner* — Richard Gurtowski
(74) *Attorney, Agent, or Firm* — Global Patent Operation; John A. Kramer

(57) ABSTRACT

Methods and systems are provided for operating a vehicle including an engine and a fuel system. In one embodiment, a water drainage system for a fuel system comprises a fuel tank, a fuel-water separator in fluid communication with the fuel tank, and a purge tank in fluid communication with the fuel-water separator and the fuel tank, the purge tank separate from the fuel tank. The water drainage system further includes a fuel property sensor for detecting a presence of water and a purge line in fluid communication with the purge tank for removing fluid from the purge tank, a flow of the fluid from the purge tank controlled by a check valve.

7 Claims, 6 Drawing Sheets

(51) Int. Cl.
  *F02N 11/08* (2006.01)
  *F02M 37/22* (2006.01)
  *F02M 35/04* (2006.01)
  *F02D 19/06* (2006.01)
  *G01N 33/28* (2006.01)

(56) References Cited

U.S. PATENT DOCUMENTS

| | | | |
|---|---|---|---|
| 4,034,335 A | 7/1977 | Harazoe et al. | |
| 4,129,501 A * | 12/1978 | Haynes | G01N 33/2847 |
| | | | 200/61.05 |
| 4,172,573 A | 10/1979 | Moore et al. | |
| 4,257,890 A | 3/1981 | Hurner | |
| 4,404,944 A * | 9/1983 | Yamazaki | F02D 19/0605 |
| | | | 123/179.15 |
| 4,637,351 A * | 1/1987 | Pakula | F02M 35/042 |
| | | | 123/25 A |
| 4,787,350 A | 11/1988 | Syassen | |
| 4,795,556 A | 1/1989 | Brotea et al. | |
| 5,305,908 A | 4/1994 | Otto et al. | |
| 6,275,759 B1 | 8/2001 | Nakajima et al. | |
| 6,444,121 B1 | 9/2002 | Maxwell | |
| 6,676,841 B2 | 1/2004 | Akins et al. | |
| 6,709,576 B2 | 3/2004 | Jokschas | |
| 6,953,527 B2 | 10/2005 | Brower et al. | |
| 7,438,042 B1 | 10/2008 | Kawada | |
| 2005/0121374 A1 | 6/2005 | Girondi | |
| 2006/0027017 A1 | 2/2006 | Kamatsuke | |
| 2006/0086649 A1 | 4/2006 | Wieczorek et al. | |
| 2008/0110812 A1 | 5/2008 | Jensen et al. | |

FOREIGN PATENT DOCUMENTS

| | | |
|---|---|---|
| WO | 03067068 A1 | 8/2003 |
| WO | 2009134192 A1 | 11/2009 |

* cited by examiner

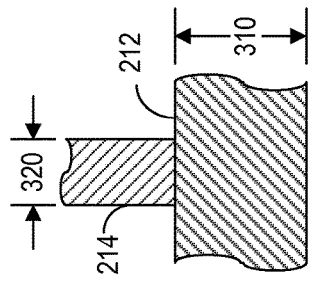
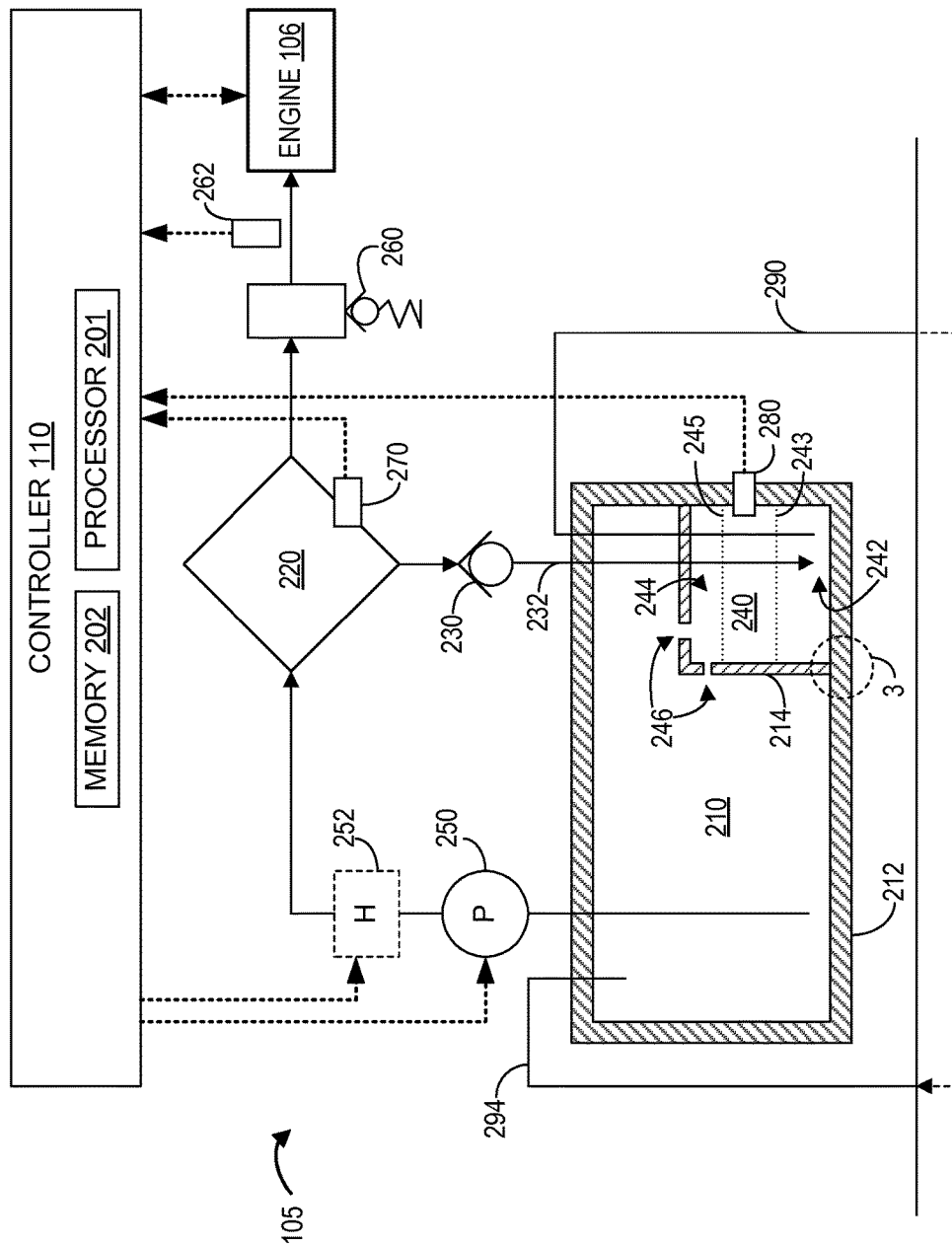

METHOD AND SYSTEM FOR WATER DRAINAGE IN FUEL SYSTEM

CROSS REFERENCE TO RELATED APPLICATIONS

This application is a continuation-in-part of U.S. patent application Ser. No. 12/859,879, entitled METHOD AND SYSTEM FOR WATER DRAINAGE IN FUEL SYSTEM, filed Aug. 20, 2010, the entirety of which is hereby incorporated herein by reference for all purposes.

FIELD

Certain embodiments of the subject matter disclosed herein relate to systems and methods for an off-highway vehicle including a fuel system.

BACKGROUND

Water may become intermixed with diesel fuel or other fuels in several ways, including purposeful mixing, condensation of humid air during transportation from refineries or other stations to end-distribution holding tanks, by leakage through faulty valves, pipes, or vents, and by careless handling. Water in fuel can cause fuel injector nozzle and pump corrosion, microorganism growth, and fuel filter plugging with materials resulting from the corrosion or microbial growth. In cold climates, ice formation in fuels containing water may cause fuel line and filter plugging degradation. Thus, various approaches are available to separate water from diesel fuel.

In one example, an off-highway vehicle, such as a locomotive or a mining truck may include a fuel-water separator for separating water from the fuel, and a purge tank for storing the separated water. The purge tank is then periodically inspected and emptied.

The inventors herein have recognized some shortcomings in such systems. For example, the required inspection interval for the purge tank may be more often than a regularly scheduled maintenance period. As such, the additional inspections for the purge tank can significantly increase maintenance costs of the vehicle. On the other hand, simply enlarging the purge tank to enable longer intervals between inspection leads to other disadvantages related to fuel system packaging, etc.

BRIEF DESCRIPTION OF THE INVENTION

Methods and systems are provided for operating an off-highway vehicle including an engine and a fuel system. In one embodiment, a water drainage system for a fuel system comprises a fuel tank, a fuel-water separator in fluid communication with the fuel tank, and a purge tank in fluid communication with the fuel-water separator and the fuel tank, the purge tank separate from the fuel tank. The water drainage system further includes a fuel property sensor for detecting a presence of water and a purge line in fluid communication with the purge tank for removing fluid from the purge tank, a flow of the fluid from the purge tank controlled by a check valve.

Thus, the water drainage system may operate with little or no manual intervention between scheduled maintenances of the off-highway vehicle.

This brief description is provided to introduce a selection of concepts in a simplified form that are further described herein. This brief description is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure. Also, the inventor herein has recognized any identified issues and corresponding solutions.

BRIEF DESCRIPTION OF THE DRAWINGS

The present invention will be better understood from reading the following description of non-limiting embodiments, with reference to the attached drawings, wherein below:

FIG. 2 shows an embodiment of a fuel system comprising a fuel tank including an exterior wall and an interior wall.

FIG. 3 shows an intersection of the interior wall with the external wall of the embodiment of the fuel tank from FIG. 2.

DETAILED DESCRIPTION

Figure 1:
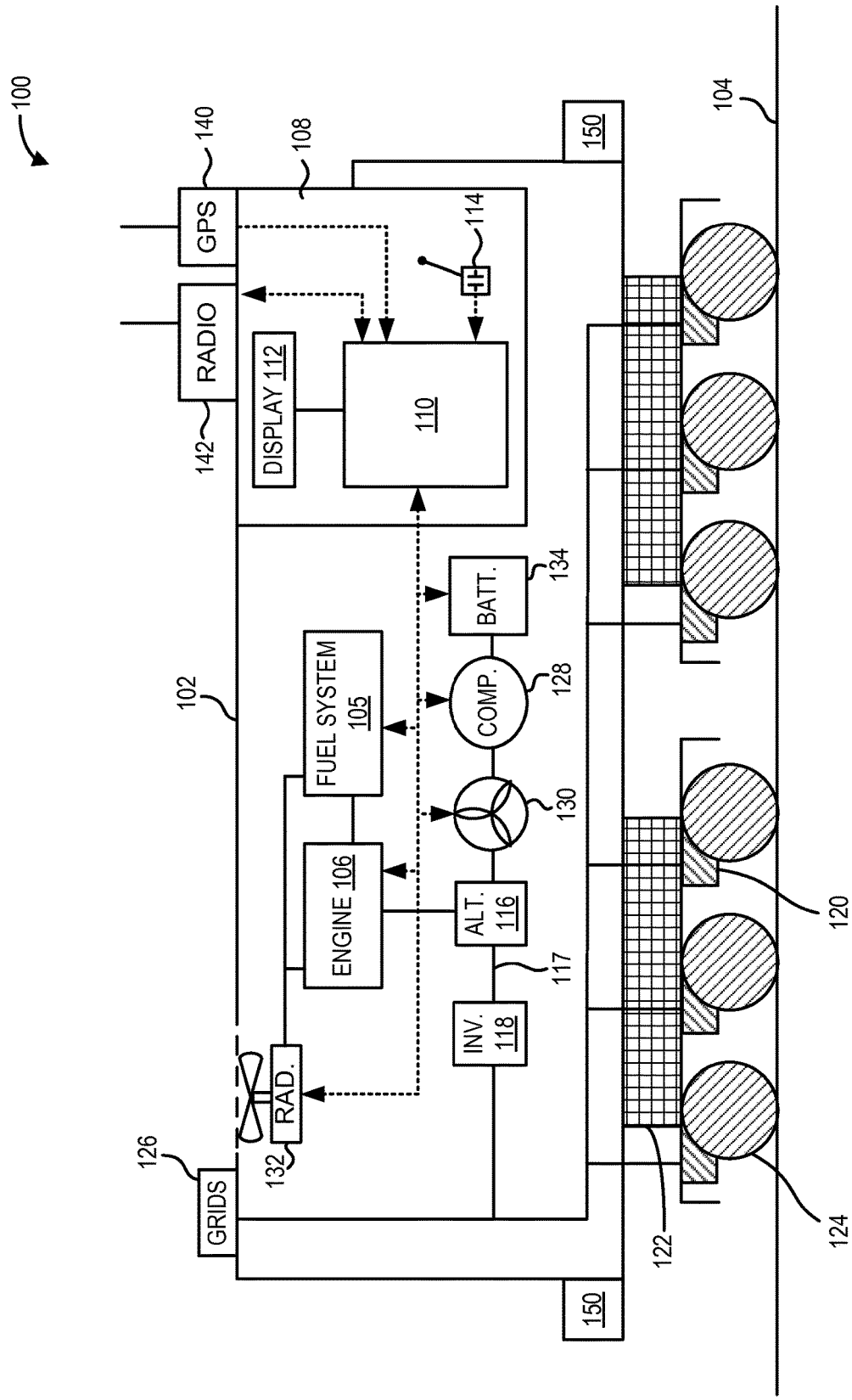
FIG. 1 shows an embodiment of a diesel-electric locomotive including a fuel system and an engine.
Figure 4:
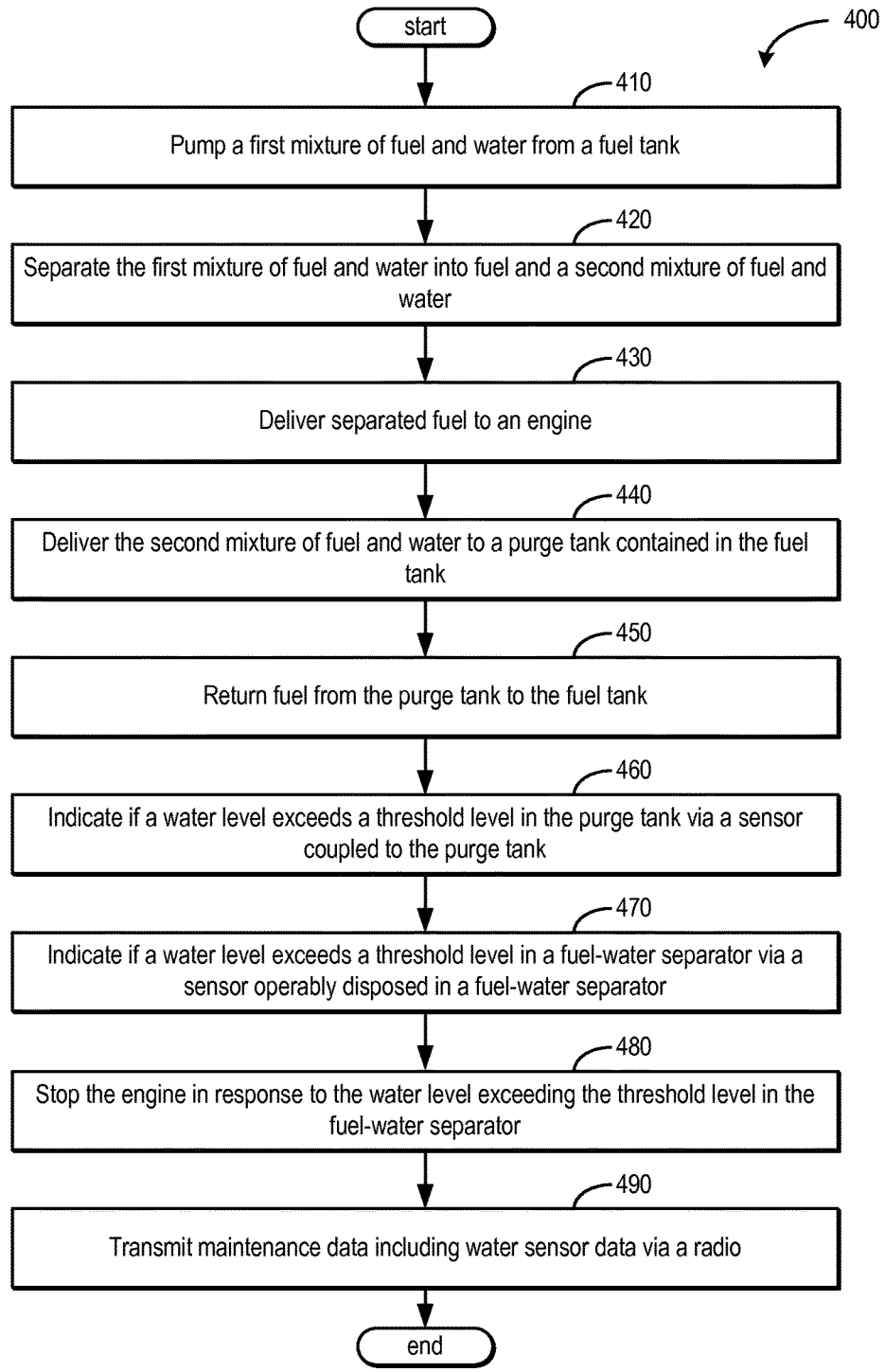
FIG. 4 shows an embodiment of a method of operating an engine.
Figure 5:
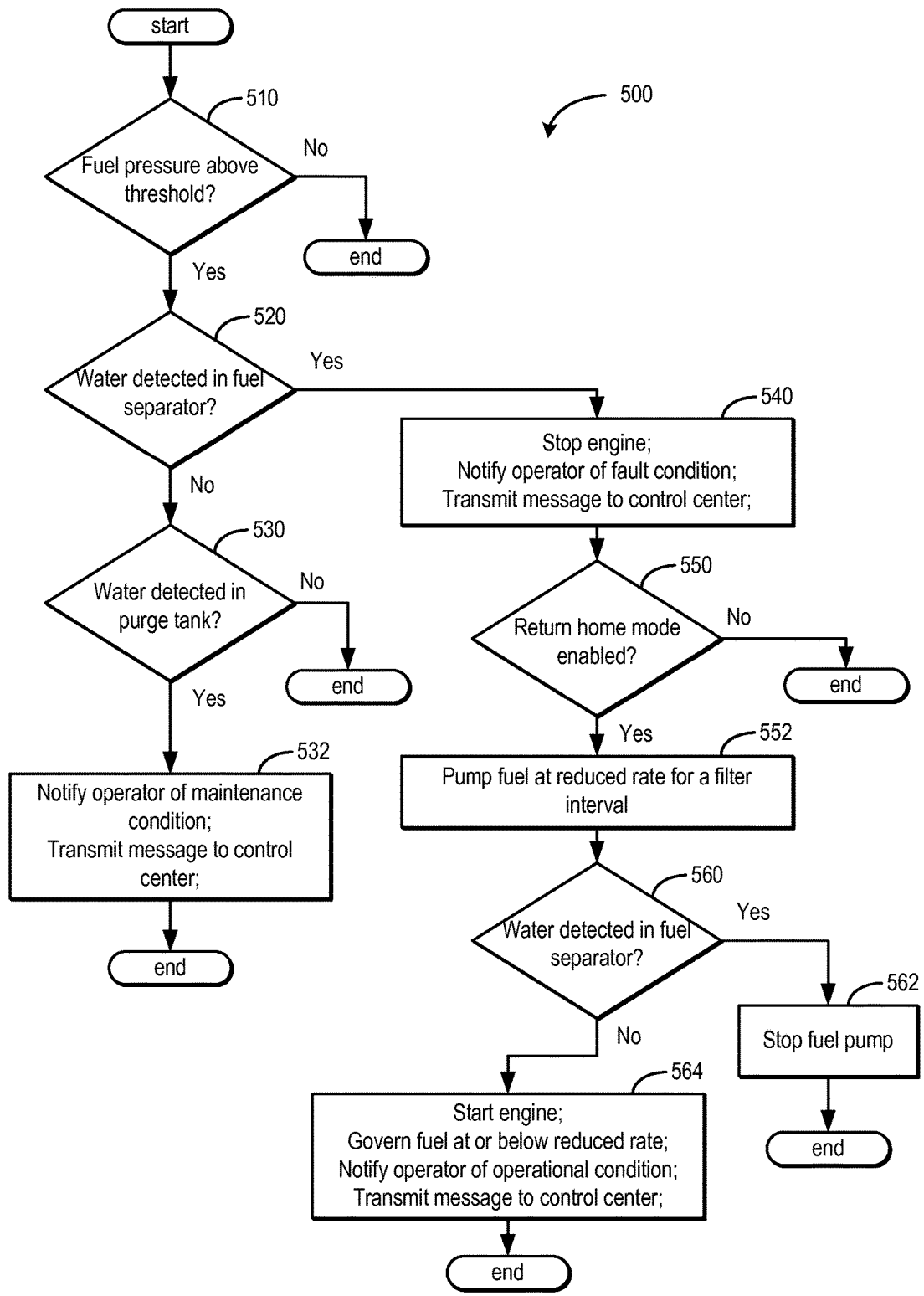
FIG. 5 shows a high level flow chart of an embodiment of a method of operating a vehicle system including an engine and a fuel system as in FIG. 2.
Figure 6:
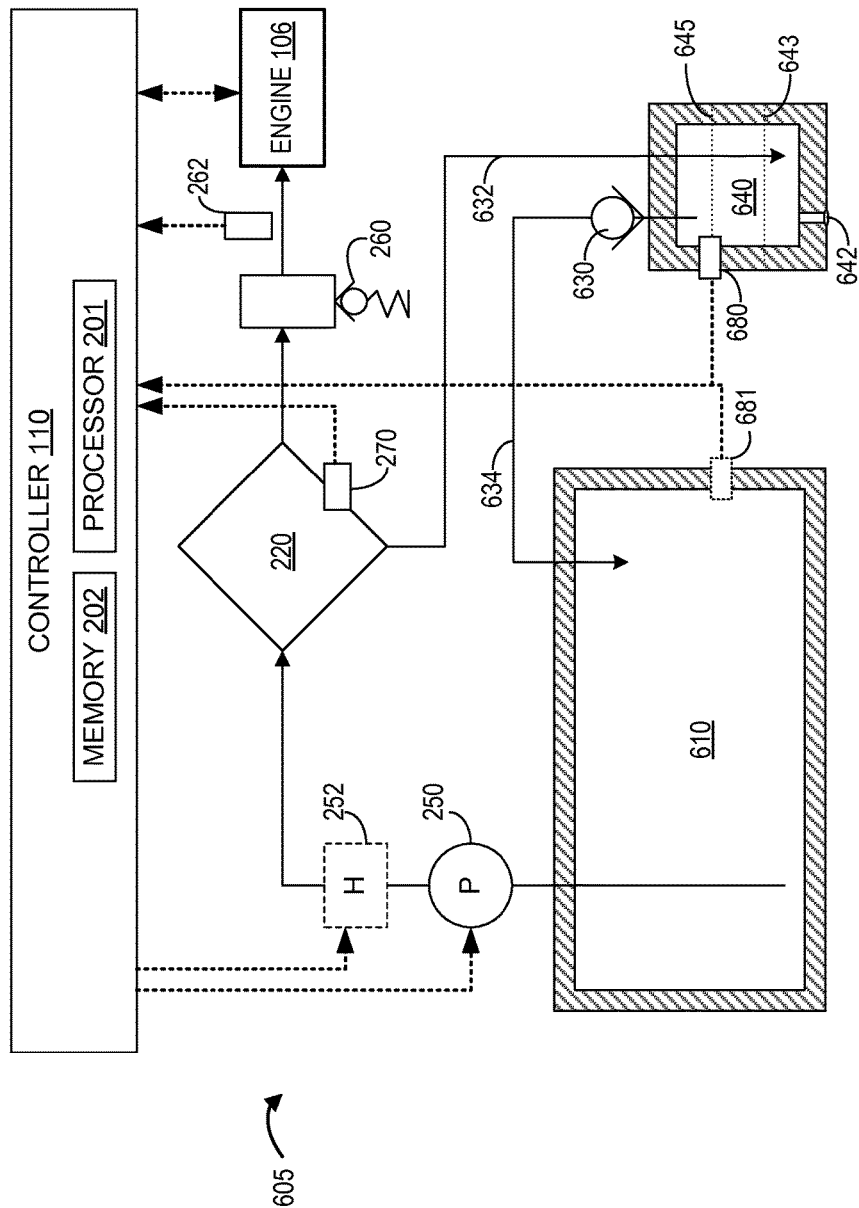
FIG. 6 shows another embodiment of a fuel system including a purge tank separate from a fuel tank.
Figure 7:
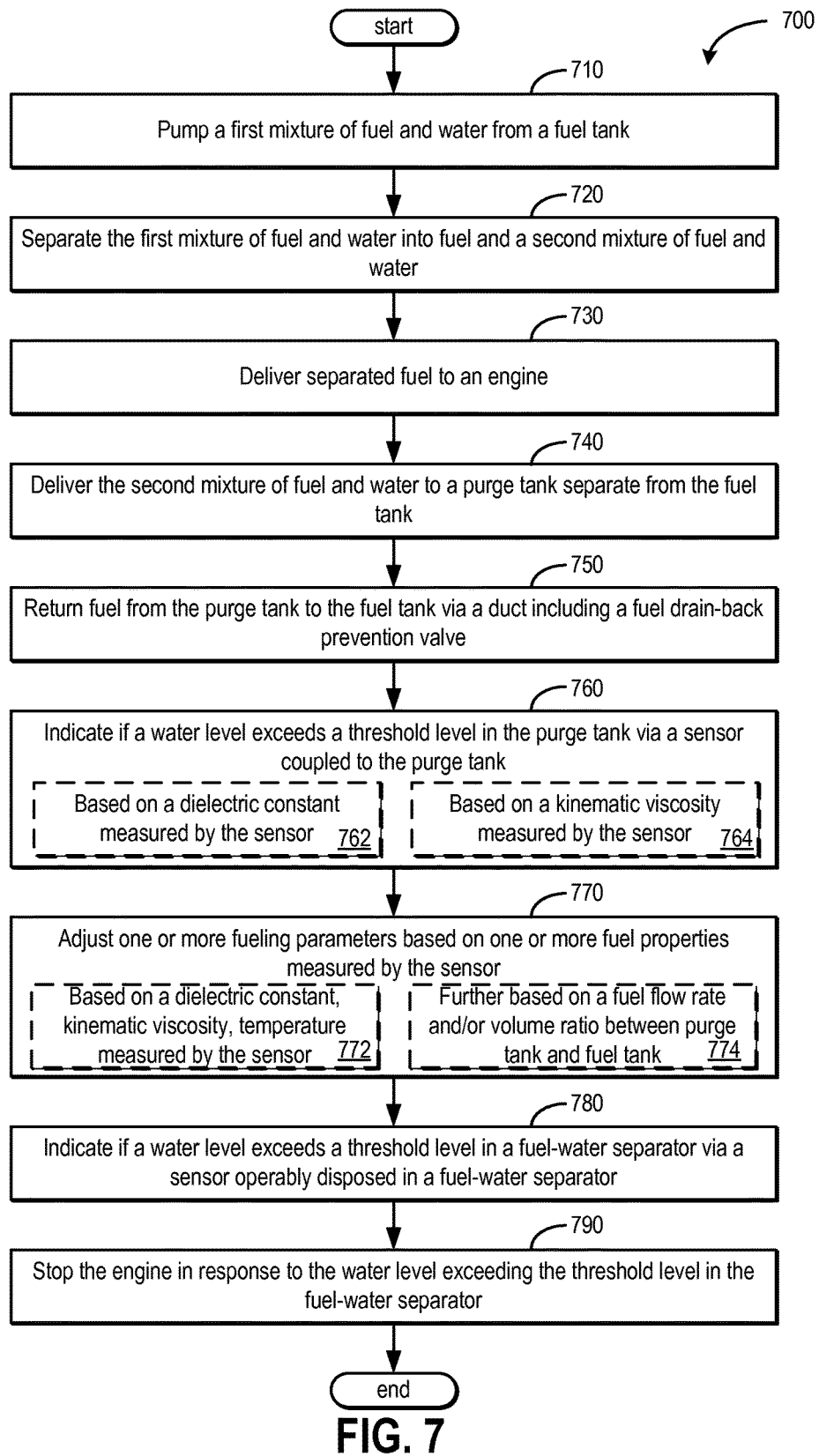
FIG. 7 shows an embodiment of a method for operating an engine including the fuel system of FIG. 6.

Off-highway vehicles, such as mining trucks or the example of a locomotive in FIG. 1, may include an engine supplied by a fuel system with a fuel tank. Fuel in the fuel tank may be intermixed with water and it may be desirable for the fuel system to separate the water and the fuel. An embodiment of a fuel system, as illustrated in FIG. 2, may include a fuel tank, a fuel-water separator, and a purge tank enclosed in the fuel tank. In one embodiment, the fuel tank may include an exterior wall and an interior wall that may intersect with the exterior wall. The interior wall may be shared between the fuel tank and the purge tank. FIG. 3 shows an intersection of the interior wall with the exterior wall. FIGS. 4 and 5 show embodiments of methods of operating a vehicle system, such as the locomotive in FIG. 1, supplied with fuel from a fuel system, such as the fuel system of FIG. 2. FIG. 6 shows another embodiment of a fuel system including a purge tank separate from a fuel tank. FIG. 7 shows an embodiment of a method for operating a vehicle system including the fuel system of FIG. 6. In this manner, water and fuel may be separated by a fuel system supplying an engine of an off-highway vehicle.

FIG. 1 is a block diagram of an example vehicle or vehicle system, herein depicted as locomotive 100, configured to run on track 104. In one example, locomotive 100 may be a diesel electric vehicle operating with a diesel engine 106 supplied with diesel fuel by a fuel system 105 located within a main engine housing 102. In other non-limiting embodiments, engine 106 may combust fuel including gasoline, kerosene, biodiesel, or other petroleum distillates of similar density. Fuel system 105, as further elaborated herein, includes a fuel-water separator for separating water out of the mixture of fuel and entrained water, or wet fuel, stored in a fuel tank. Thus, fuel with little or no water, or dry fuel, may be delivered to engine 106 and the separated water may be delivered to and stored in a purge tank of the fuel system. The fuel tank may be structurally enhanced to resist punctures and deformation. Straps and/or a protective cage may secure the fuel tank to main engine housing 102. The purge tank may be similarly structurally enhanced, or alternatively, the purge tank may be contained in the fuel tank so that the structural enhancements of the fuel tank may also benefit the purge tank.

Locomotive operating crew and electronic components involved in locomotive systems control and management, for example controller 110, may be housed within a locomotive cab 108. In one example, controller 110 may include a computer control system. The locomotive control system may further comprise computer readable storage media including code for enabling an on-board monitoring of locomotive operation. Controller 110, overseeing locomotive systems control and management, may be configured to receive signals from a variety of sensors, as further elaborated herein, in order to estimate locomotive operating parameters. For example, controller 110 may estimate geographic coordinates of locomotive 100 using signals from a Global Positioning System (GPS) radio receiver 140. Controller 110 may be further linked to display 112, such as a diagnostic interface display, providing a user interface to the locomotive operating crew. Controller 110 may control the engine 106, in response to operator input, by sending a command to various engine control hardware components such as inverters 118, alternator 116, relays, fuel injectors, fuel pumps (not shown in FIG. 1), etc. For example, the operator may select a power output for the locomotive by operating a throttle control 114.

Controller 110 and/or a locomotive operator may communicate with a control center via radio 142. As non-limiting examples, radio 142 may include a VHF radio, a cell radio, an 802.11 radio, and combinations thereof. The locomotive operator may communicate with the control center by sending and receiving voice and/or text messages via radio 142. Additionally, controller 110 may communicate with the control center by sending and receiving data messages. For example, controller 110 may transmit maintenance data and/or engine operational status to the control center via radio 142.

Engine 106 may be started with an engine starting system. In one example, a generator start may be performed wherein the electrical energy produced by a generator or alternator 116 ("ALT") may be used to start engine 106. Alternatively, the engine starting system may comprise a motor, such as an electric starter motor, or a compressed air motor, for example. It will also be appreciated that the engine may be started using energy in a battery system, or other appropriate energy sources.

The diesel engine 106 generates a torque that is transmitted to an alternator 116 along a drive shaft (not shown). The generated torque is used by alternator 116 to generate electricity for subsequent propagation of the vehicle. The electrical power may be transmitted along an electrical bus 117 to a variety of downstream electrical components. Based on the nature of the generated electrical output, the electrical bus may be a direct current (DC) bus (as depicted) or an alternating current (AC) bus.

Alternator 116 may be connected in series to one, or more, rectifiers (not shown) that convert the alternator's electrical output to DC electrical power prior to transmission along the DC bus 117. Based on the configuration of a downstream electrical component receiving power from the DC bus, one or more inverters 118 ("INV") may be configured to invert the electrical power from the electrical bus prior to supplying electrical power to the downstream component. In one embodiment of locomotive 100, a single inverter 118 may supply AC electrical power from a DC electrical bus to a plurality of components. In an alternate embodiment, each of a plurality of distinct inverters may supply electrical power to a distinct component.

A traction motor 120, mounted on a truck 122 below the main engine housing 102, may receive electrical power from alternator 116 through the DC bus 117 to provide traction power to propel the locomotive. As described herein, traction motor 120 may be an AC motor. Accordingly, an inverter paired with the fraction motor may convert the DC input to an appropriate AC input, such as a three-phase AC input, for subsequent use by the traction motor. In alternate embodiments, traction motor 120 may be a DC motor directly employing the output of the alternator 116 after rectification and transmission along the DC bus 117. One example locomotive configuration includes one inverter/traction motor pair per wheel-axle 124. As depicted herein, six pairs of inverter/traction motors are shown for each of six pairs of wheel-axle of the locomotive. Traction motor 120 may also be configured to act as a generator providing dynamic braking to brake locomotive 100. In particular, during dynamic braking, the traction motor may provide torque in a direction that is opposite from the rolling direction, thereby generating electricity that is dissipated as heat by a grid of resistors 126 connected to the electrical bus. In one example, the grid includes stacks of resistive elements connected in series directly to the electrical bus. The stacks of resistive elements may be positioned proximate to the ceiling of main engine housing 102 in order to facilitate air cooling and heat dissipation from the grid.

Air brakes (not shown) making use of compressed air may be used by locomotive 100 as part of a vehicle braking system. The compressed air may be generated from intake air by compressor 128 ("COMP"). A multitude of motor driven airflow devices may be operated for temperature control of locomotive components. The airflow devices may include, but are not limited to, blowers, radiators, and fans. A variety of blowers 130 may be provided for the forced-air cooling of various electrical components. For example, a fraction motor blower to cool traction motor 120 during periods of heavy work. Engine temperature is maintained in part by a radiator 132 ("RAD"). A cooling system comprising a water-based coolant may optionally be used in conjunction with the radiator 132 to provide additional cooling of the engine. The hot water-based coolant from the engine may also be used to heat fuel in fuel system 105.

An on-board electrical energy storage device, represented by battery 134 ("BATT") in this example, may also be linked to DC bus 117. A DC-DC converter (not shown) may be configured between DC bus 117 and battery 134 to allow the high voltage of the DC bus (for example in the range of 1000V) to be stepped down appropriately for use by the battery (for example in the range of 12-75V). In the case of a hybrid locomotive, the on-board electrical energy storage device may be in the form of high voltage batteries, such that the placement of an intermediate DC-DC converter may not be necessitated. The battery may be charged by running engine 106. The electrical energy stored in the battery may be used during a stand-by mode of engine operation, or when the engine is shut down, to operate various electronic components such as lights, on-board monitoring systems, microprocessors, displays, climate controls, and the like. Battery 134 may also be used to provide an initial charge to start-up engine 106 from a shut-down condition. In alternate embodiments, the electrical energy storage device may be a super-capacitor, for example.

Locomotive 100 may be coupled to a vehicle, such as another locomotive or a railroad car, with a coupling device, such as coupler 150. Locomotive 100 may include one or more couplers to couple with one or more vehicles in a series of vehicles. In one example, a first locomotive may be connected to a second locomotive with coupler 150. A controller in the first locomotive, such as controller 110, may be configured to receive and transmit information to a controller in the second locomotive. The information may include the position or order of a series of locomotives, for example. As non-limiting examples, the information may be transmitted by radio 142 over a wireless network or an electrical cable connecting each locomotive. In this manner, a locomotive may communicate information such as engine and/or vehicle operating conditions to one or more other locomotives.

Returning to fuel system 105, FIG. 2 illustrates an embodiment of fuel system 105. Fuel system 105 comprises a fuel tank 210, a fuel-water separator 220, a drain valve 230, and a purge tank 240. Fuel-water separator 220 is in fluid communication with fuel tank 210. In one embodiment, fuel entrained with water is pumped from fuel tank 210 by a pump 250 to fuel-water separator 220. An optional fuel heater 252 may be interposed between fuel tank 210 and fuel-water separator 220. In an alternate embodiment, fuel heater 252 may be coupled to fuel tank 210. In one embodiment, fuel heater 252 may transfer thermal energy from the cooling system to the fuel. For example, thermal energy from hot water-based coolant may be used to heat fuel in fuel system 105. Controller 110 may be used to control operation of pump 250 and heater 252.

Fuel-water separator 220 receives a mixture of fuel and water from fuel tank 210 and separates the mixture into dry fuel and purge liquid. The purge liquid may include fuel, water, or a water-fuel emulsion. The dry fuel may be delivered to engine 106. In one embodiment, fuel-water separator 220 is in fluid communication with a fuel pressure regulating valve 260 which is in fluid communication with engine 106. Thus, fuel may flow from an outlet port of fuel-water separator 220 through pressure regulating valve 260 to engine 106. Fuel pressure regulating valve 260 may include a check valve with a set point pressure less than or equal to a peak fuel pressure of engine 106. If the fuel pressure of fuel pressure regulating valve 260 is less than the set point pressure, fuel pressure regulating valve 260 may remain closed and all fuel from fuel-water separator 220 may be delivered to engine 106. However, if the fuel pressure of fuel pressure regulating valve 260 is greater than or equal to the set point pressure, fuel pressure regulating valve 260 may open and some fuel from fuel-water separator 220 may be diverted away from engine 106. Opening pressure regulating valve 260 may reduce the fuel pressure of fuel being delivered to engine 106 so that fuel pressure may be maintained at less than or equal to the peak fuel pressure of engine 106. In one embodiment, pressure regulating valve 260 may return fuel to fuel tank 210 when pressure regulating valve 260 is open. In one embodiment, the fuel pressure to engine 106 may be measured with a pressure sensor 262 and the pressure may be communicated to controller 110.

Fuel-water separator 220 may include a separator water sensor 270 operably disposed in fuel-water separator 220 for detecting the presence of water. Fuel-water separator 220 is a vessel, having an interior volume, which is capable of holding liquids (e.g. fuel and/or water) in a generally leak proof and watertight manner. Separator water sensor 270 may be positioned in the interior of fuel-water separator 220. Although referred to as a "water" sensor, separator water sensor 270 is more specifically a water-in-fuel sensor, that is, a sensor configured and able to detect water in the presence of fuel. Separator water sensor 270 is electrically connected to controller 110, and outputs a signal to controller 110 for indicating whether water is present at the sensor tip or other active sensor portion of separator water sensor 270 where water is detected. Separator water sensor 270 is considered as being dry if no water is detected at the sensing tip; exposure to air or liquid fuel (without water present) would be considered dry conditions.

Fuel-water separator 220 is in fluid communication with drain valve 230 which is in fluid communication with purge tank 240. Drain valve 230 may receive the purge liquid from an outlet port of fuel-water separator 220. Drain valve 230 may include a check valve with a set point pressure less than the set point pressure of the fuel pressure regulating valve. Additionally, drain valve 230 may have a set point pressure greater than a priming pressure of engine 106. In one embodiment, the set point pressure of drain valve 230 may be less than half of the set point pressure of fuel pressure regulating valve 260. In another embodiment, the set point pressure of drain valve 230 may be between ten percent and fifty percent of the set point pressure of fuel pressure regulating valve 260. When fuel pressure is less than the set point pressure of drain valve 230 (e.g. drain valve 230 is closed), the purge liquid may not flow from fuel-water separator 220 and fuel pressure may increase faster than if drain valve 230 were open. When fuel pressure is greater than or equal to the set point pressure of drain valve 230 (e.g. drain valve 230 is open), the purge liquid may flow from fuel-water separator 220 to purge tank 240.

Drain valve 230 may further include an orifice for limiting flow from fuel-water separator 220 to purge tank 240. The size of the orifice may control a maximum flow rate through the orifice and drain valve 230. For example, increasing the size of the orifice may increase flow through drain valve 230 and decrease fuel pressure. Alternatively, decreasing the size of the orifice may decrease flow through the orifice and drain valve 230 and increase fuel pressure.

Purge tank 240 is in fluid communication with drain valve 230 and fuel tank 210. In one embodiment, the purge liquid may flow from drain valve 230 through a duct 232 with an outlet near a bottom 242 of purge tank 240. For example, a lateral plane 243 may be defined as a plane cutting horizontally across purge tank 240 when purge tank 240 is positioned in its designated orientation for normal use. Near the bottom 242 of purge tank 240 may be defined as below lateral plane 243. The purge liquid is received near the bottom 242 of purge tank 240. The purge liquid may include a mixture of fuel and water which may be separated in purge tank 240. For example, water may have a greater density than fuel and so water may preferentially sink toward the bottom 242 of purge tank 240 and fuel may preferentially rise toward a top 244 of purge tank 240. In one example, near the top 244 of purge tank 240 may be defined as a lateral plane 245 cutting horizontally across purge tank 240, parallel with lateral plane 243. In one embodiment, purge tank 240 may be enclosed in fuel tank 210 and purge tank 240 may include one or more holes 246 near the top 244 of purge tank 240. Liquid may flow from purge tank 240 through one or more holes 246 into fuel tank 210. When fuel is less dense than water, the fuel may flow through the one or more holes 246 near the top 244 of purge tank 240 and water may be stored near the bottom 242 of purge tank 240. As water flows into purge tank 240 the level of the water may rise from the bottom 242 toward the top 244 of purge tank 240. An area of the one or more holes 246 may be greater than or equal to an area of the orifice of drain valve 230. In other words, the total area of all of the one or more holes 246 may be greater than or equal to an area of the orifice of drain valve 230. Thus, a maximum flow rate through the one or more holes 246 may be greater than or equal to a maximum flow rate through the orifice of drain valve 230. In an alternate embodiment, the area of each one or more holes 246 may be greater than or equal to an area of the orifice of drain valve 230.

An interior volume of purge tank 240 may be large enough for locomotive 100 to operate for an extended period without filling purge tank 240 with water. In one embodiment, the volume of purge tank 240 may be greater than or equal to the volume of water to be extracted from fuel when locomotive 100 is operated under typical or worst-case conditions between scheduled maintenance periods, such as a period of 180 days. For example, the volume of purge tank 240 may be sized according to average fuel consumption (e.g. miles per gallon) of locomotive 100, an average distance to be travelled by locomotive 100, and an average water content of fuel. In another example, the volume of purge tank 240 may be sized according to worst-case fuel consumption of locomotive 100, a worst-case distance to be travelled, and a worst-case water content of fuel. In this manner, purge tank 240 may not fill up with water between scheduled maintenance periods of locomotive 100. However, some conditions may lead to purge tank 240 filling with water before the maintenance period. For example, out of specification fuel (e.g. fuel with a water concentration in excess of the specified amount), water leaking into fuel system 105, and increased fuel consumption (e.g. burning more fuel and extracting more water) may result in purge tank 240 filling more quickly than expected.

Thus, a purge tank water sensor 280 may be operably coupled to purge tank 240 for detecting when purge tank 240 is at or near its water holding capacity. Specifically, purge tank water sensor 280 may be operably coupled to purge tank 240 for detecting the presence of water in fuel. Similar to separator water sensor 270, purge tank water sensor 280 is considered as being dry if no water is detected at the sensing tip; exposure to air or liquid fuel (without water present) would be considered dry conditions. If purge tank water sensor 280 is mounted at a pre-determined height above the bottom 242 of purge tank 240, a threshold volume of water in purge tank 240 may be determined by calculating the volume of the water column that rises to the height of purge tank water sensor 280. In one embodiment, purge tank water sensor 280 may be operably coupled to purge tank 240 above lateral plane 243. In other words, purge tank water sensor 280 may be mounted above the outlet for receiving purge liquid. In another embodiment, purge tank water sensor 280 may be operably coupled to purge tank 240 above lateral plane 243 and below lateral plane 245. In other words, purge tank water sensor 280 may be mounted above the outlet for receiving purge liquid and below the one or more holes 246 of purge tank 240. Mounting purge tank water sensor 280 nearer the top 244 of purge tank 240 may allow more water to be held in purge tank 240 than if purge tank water sensor 280 is mounted nearer the bottom 242 of purge tank 240. Thus, purge tank water sensor 280 may be mounted above a mid-point of purge tank 240. Purge tank water sensor 280 is electrically connected to controller 110 and outputs a signal to controller 110 for indicating whether water is present at the sensor tip or other active sensor portion of purge tank water sensor 280 where water is detected. In other words, purge tank water sensor 280 may indicate to controller 110 when water in purge tank 240 exceeds a threshold amount of water which may be near the water holding capacity of purge tank 240.

As further elaborated herein, the output signals from separator water sensor 270 and purge tank water sensor 280 may be processed by controller 110 for the technical effect of controlling engine 106 and fuel system 105. In one embodiment, controller 110 includes a processor 201 and a computer readable medium, such as memory 202. Instructions configured to execute on processor 201 may be encoded and stored in memory 202. For example, instructions may be configured to detect if water stored in purge tank 240 exceeds a threshold amount via purge tank water sensor 280. As another example, instructions may be configured to detect if water exceeds a threshold amount of water in fuel-water separator 220 via separator water sensor 270. Further examples of instructions that may be encoded in controller 110 are described with regard to the methods of FIGS. 4-5, which may be routines carried out by controller 110.

During maintenance, water may be removed from purge tank 240 via a purge port 290 in fluid communication with purge tank 240. In one embodiment, purge port 290 may include a suction line having an inlet near the bottom 242 of purge tank 240. In this manner, water near the bottom 242 of purge tank 240 may be removed before fuel and/or water near the top 244 of purge tank 240. Purge port 290 may be different from duct 232 to enable water to be removed from purge tank 240 without disconnecting duct 232 from drain valve 230. During maintenance, purge port 290 may be connected to an inlet of a fuel polishing cart 292 ("FUEL POLISHER") and a fill port 294 of fuel tank 210 may be connected to an outlet of fuel polishing cart 292. Fuel polishing cart 292 may pump liquid (e.g. water and/or fuel) from purge tank 240 via purge port 290, filter (e.g. polish) the liquid, and return dry fuel to fuel tank 210 via fill port 294. In this manner, water may be removed from purge tank 240 without removing purge tank 240 from fuel tank 210. In an alternate embodiment, locomotive 100 may include fuel polishing cart 292 and liquid from purge tank 240 may be filtered when locomotive 100 is idle, for example.

Purge tank 240 may be enclosed within fuel tank 210. In one embodiment, fuel tank 210 may include one or more exterior walls, such as exterior wall 212, and one or more interior walls, such as interior wall 214. The one or more exterior walls may enclose the volume of fuel tank 210 and the one or more interior walls may form one or more compartments within fuel tank 210. For example, one compartment may form purge tank 240. In other words, purge tank 240 may share one or more walls with fuel tank 210. For example, wall 214 may be an interior wall of fuel tank 210 and a wall of purge tank 240, and wall 212 may be an exterior wall of fuel tank 210 and a wall of purge tank 240. The one or more interior walls may include one or more holes 246 extending through the one or more interior walls for fluid to flow between purge tank 240 and fuel tank 210.

FIG. 3 shows an embodiment of an intersection of interior wall 214 with external wall 212 of fuel tank 210. Fuel tank 210 may be structurally enhanced to resist punctures and deformation. In one embodiment, external walls of fuel tank 210 may be constructed of heavy-gauge steel. Increasing the thickness of the external walls may increase the resistance to deformation and/or puncturing. However, increasing the thickness of the external walls may also increase the weight of locomotive 100 which may result in higher fuel consumption. It may also be desirable for purge tank 240 to resist deformation and punctures. Enclosing purge tank 240 within the one or more thick external walls of fuel tank 210 may protect purge tank 240 from deformation and/or punctures. Thus, internal walls of purge tank 240 (and fuel tank 210) may be thinner than external walls of fuel tank 210. In one embodiment, a thickness 310 of external wall 212 may be greater than twice as thick as a thickness 320 of internal wall 214. In an alternate embodiment, thickness 310 of external wall 212 may be greater than five times as thick as thickness 320 of internal wall 214. In yet another alternate embodiment, thickness 310 of external wall 212 may be less than five times as thick as thickness 320 of internal wall 214 and greater than twice as thick as thickness 320 of internal wall 214.

FIG. 4 shows an embodiment of a method 400 of operating a vehicle, such as locomotive 100. At 410, a first mixture of fuel and water may be pumped from a fuel tank. For example, pump 250 may pump fuel entrained with water from fuel tank 210. In one embodiment, the fuel and water may be heated with a heater, such as heater 252. At 420, the first mixture of fuel and water may be separated into fuel and a second mixture of fuel and water. For example, fuel-water separator 220 may separate the fuel entrained with water into dry fuel and purge liquid. The purge liquid may include a second mixture of fuel and water, where the water is less emulsified in the fuel.

At 430, the separated dry fuel may be delivered to the engine. For example, dry fuel may flow from fuel-water separator 220 through fuel pressure regulating valve 260 to engine 106. Fuel pressure regulating valve 260 may limit the fuel pressure of the dry fuel to less than a peak fuel pressure of engine 106.

At 440, the second mixture of fuel and water may be delivered to a purge tank contained in the fuel tank. For example, the purge liquid may be delivered to purge tank 240 contained in fuel tank 210. In one embodiment, the purge liquid may be received in purge tank 240 via an outlet of duct 232 near the bottom 242 of purge tank 240. In one embodiment, the second mixture of fuel and water may be delivered to the purge tank if fuel pressure exceeds a priming pressure of the engine. For example, drain valve 230 may be closed when fuel pressure is less than the priming pressure of engine 106 and drain valve 230 may be open when fuel pressure is greater than or equal to the priming pressure of engine 106. In one embodiment, the priming pressure may be between ten percent and fifty percent of the peak fuel pressure.

At 450, fuel may be returned from the purge tank to the fuel tank. For example, water, having a greater density than fuel, may remain near the bottom 242 of purge tank 240 and fuel may rise to near the top 244 of purge tank 240. When purge tank 240 is full of water and fuel, and when purge liquid enters purge tank 240 through duct 232, fuel may flow through one or more holes 246 back to fuel tank 210.

At 460, a sensor coupled to the purge tank may indicate if water exceeds a threshold level in the purge tank. For example, purge tank water sensor 280 may indicate to controller 110 when water reaches the level of purge tank water sensor 280. During typical operation of locomotive 100, water may remain below the threshold level of purge tank 240. However, out-of-specification fuel having too much water, water leaks into fuel system 105, increased fuel consumption of locomotive 100, or delayed maintenance may lead to water in purge tank 240 exceeding a threshold level. During maintenance of locomotive 100, water may be removed from purge tank 240 via purge line 290, for example. Locomotive operational data and the indication from purge tank water sensor 280 may be used to diagnose potential sources of water in purge tank 240. For example, location data from GPS radio receiver 140 and data from a fuel level sensor may be used to record each filling location for locomotive 100. Excessive water content, as indicated by purge tank water sensor 280, may be correlated with the filling locations of locomotive 100 to diagnose where out-of-specification fuel may be present. As another example, water may leak from an engine component, such heater 252, into the fuel. If purge tank water sensor 280 indicates water is present earlier than expected, then additional diagnostics may be performed to identify whether one or more engine components are faulty.

At 470, a sensor operably disposed in the fuel-water separator may indicate if water exceeds a threshold level in a fuel-water separator. For example, separator water sensor 270 may indicate to controller 110 when water exceeds the threshold level in fuel-water separator 220. In one example, water may be detected if the concentration of water in fuel being pumped from fuel tank 210 exceeds the capacity of water to be separated in fuel-water separator 220. For example, the rate of water flowing into fuel-water separator 220 may exceed the rate of purge liquid flowing from fuel-water separator 220 through drain valve 230. In one example, drain valve 230, duct 232, and/or one or more holes 246 may be clogged and the flow of purge liquid may be reduced.

At 480, the engine may be stopped if water exceeds the threshold level in the fuel-water separator. For example, separator water sensor 270 may indicate to controller 110 that water exceeds the threshold level in fuel-water separator 220, and controller 110 may stop engine 106 in response thereto. Thus, engine 106 may be protected from undesirable effects of combusting fuel mixed with water. At 490, maintenance data including water sensor data may be transmitted via a radio. For example, a maintenance message may be transmitted via radio 142 in response to separator water sensor 270 indicating water exceeds the threshold level in fuel-water separator 220. As another example, a status message may be transmitted via radio 142 if purge tank water sensor 280 indicates water exceeds the threshold level in purge tank 240. In one embodiment, maintenance and/or status messages may be transmitted to a control center via a VHF or cell radio. Alternatively or additionally, maintenance and/or status messages may be transmitted to another locomotive connected to locomotive 100 by coupler 150 and linked by an 802.11 radio.

Accordingly, a vehicle system may include fuel system 105, engine 106, and controller 110. Controller 110 may be programmed to operate the vehicle system with an embodiment of a method, such as method 500, illustrated in FIG. 5. At 510, it may be determined if fuel pressure is above a threshold. For example, fuel pressure may be measured by a sensor, such as pressure sensor 262, and compared to a threshold pressure, such as the priming pressure of engine 106. If fuel pressure is less than the threshold pressure, then the method may end. Otherwise, the pressure is greater than or equal to the threshold pressure and the method may continue at 520.

At 520, it may be determined if water is detected in fuel-water separator 220. For example, separator water sensor 270 may indicate to controller 110 when water exceeds the threshold level in fuel-water separator 220. If water exceeds the threshold level, then the method may continue at 540. If water does not exceed the threshold level, then dry fuel may be delivered to engine 106 and the method may continue at 530.

At 530, it may be determined if water is detected in purge tank 240. For example, purge tank water sensor 280 may indicate to controller 110 when water exceeds the threshold level in purge tank 240. If water does not exceed the threshold level, then the purge tank is not full and the method may end. If water exceeds the threshold level, purge tank 240 may be at or near water capacity and may need to be emptied soon. The method continues at 532 if water exceeds the threshold level.

At 532, an operator of locomotive 100 may be notified of a maintenance condition. Specifically, the operator may be notified that purge tank 240 is at or near water capacity and may need to be drained. In one embodiment, controller 110 may notify the operator via a visual and/or auditory signal on display 112. Additionally, an automated message may be transmitted to a control center indicating that water in purge tank 240 exceeds the threshold level. In one example, locomotive 100 may be brought in for maintenance when water in purge tank 240 exceeds the threshold level. In another example, locomotive 100 may continue to operate if a scheduled maintenance is within a pre-determined time or mileage of locomotive 100. The method ends after 532.

At 540, water is detected in fuel-water separator 220 and water may be delivered to engine 106 if engine 106 continues to operate. Thus, engine 106 may be stopped to prevent water from being delivered to engine 106. The operator of locomotive 100 may be notified via a visual and/or auditory signal on display 112. An automated message may be transmitted via radio 142 indicating that water is detected in fuel-water separator 220. In one example, a message requesting maintenance may be transmitted to a control center via radio 142. In another example, a status message may be transmitted to another locomotive coupled to locomotive 100 via coupler 150. The method continues at 550.

At 550, it is determined if "return home" mode is enabled. For example, stopping engine 106 of locomotive 100 in a remote location may be undesirable since the operator of locomotive 100 may be stranded and maintenance may be more difficult in a remote location. Thus, a return home mode may be configured to restart engine 106 if dry fuel can be delivered to engine 106. However, locomotive 100 may be connected to one or more other locomotives via couplers 150 and it may be more desirable to stop engine 106 than to risk operating engine 106 with fuel that may be mixed with water. In one embodiment, return home mode may be disabled if locomotive 100 is connected to one or more locomotives. If return home mode is not enabled, the method may end. If return home mode is enabled, the method may continue at 552.

At 552, engine 106 is stopped and fuel may be pumped by pump 250 at a reduced rate for a pre-determined filter interval. For example, drain valve 230, duct 232, and/or one or more holes 246 may be partially clogged which may reduce the rate of flow of purge liquid from fuel-water separator 220. In another example, the concentration of water mixed with fuel from fuel tank 210 may exceed the concentration of water that may be separated by fuel-water separator 220 when fuel is pumped near a peak flow rate. Thus, pumping fuel at a reduced rate of flow may enable fuel-water separator 220 to separate the water and to deliver dry fuel to engine 106. In one example, a filter interval may be selected such that flow through fuel-water separator 220 is at a steady-state operating point. The method may continue at 560.

At 560, it may be determined if water is detected in fuel-water separator 220. For example, separator water sensor 270 may indicate to controller 110 whether water is present above a threshold amount in fuel-water separator 220. If water is detected by separator water sensor 270, then dry fuel cannot be delivered to engine 106 at the reduced flow rate and the method continues at 562. At 562, the fuel pump is stopped and then the method ends. However, if water is not detected by separator water sensor 270, then dry fuel may be delivered to engine 106 and the method may continue at 564.

At 564, engine 106 may be started and fuel delivered to engine 106 may be governed to a rate at or below the reduced rate of flow of 552. The operator of the locomotive may be notified that locomotive 100 may be operated at a reduced rate of fuel via a visual or auditory signal on display 112. An automated message may be transmitted to a control center via radio 142 indicating that locomotive 100 may be returning for maintenance. In this manner, locomotive 100 may be moved from a remote location to a shop for maintenance. The method ends after 564.

FIG. 6 illustrates a fuel system 605 according to an alternate embodiment of the invention. Fuel system 605 may be similar to fuel system 105 and as such may be included in locomotive 100 in place of fuel system 105. Fuel system 605 includes similar elements as fuel system 105. As such, components previously introduced in FIG. 2 are numbered similarly in FIG. 6 and not reintroduced.

Similar to fuel system 105, fuel system 605 includes a fuel-water separator 220 in fluid communication with fuel tank 610, purge tank 640, and engine 106. Fuel-water separator 220 receives fuel (which may include a mixture of fuel and water) from a fuel tank 610 via pump 250 and optional heater 252. Fuel-water separator 220 separates dry fuel (e.g., fuel that does not include any appreciable water or other liquids) from water and/or water-fuel mixture, as explained above. The dry fuel is then provided to engine 106 for combustion. The water and/or water-fuel mixture from fuel-water separator 220 is drained to a purge tank 640 positioned outside of and separately from fuel tank 610.

In one embodiment, the purge liquid may flow from fuel-water separator 220 through a duct 632 with an outlet near a bottom of purge tank 640. For example, a lateral plane 643 may be defined as a plane cutting horizontally across purge tank 640 when purge tank 640 is positioned in its designated orientation for normal use. Near the bottom of purge tank 640 may be defined as below lateral plane 643. The purge liquid is received near the bottom of purge tank 640. The purge liquid may include a mixture of fuel and water which may be separated in purge tank 640. For example, water may have a greater density than fuel and so water may preferentially sink toward the bottom of purge tank 640 and fuel may preferentially rise toward a top of purge tank 640. In one example, near the top of purge tank 640 may be defined as a lateral plane 645 cutting horizontally across purge tank 640, parallel with lateral plane 643. Liquid may flow from purge tank 240 through one or more holes 246 into fuel tank 210.

When fuel is less dense than water, fuel may rise to near the top of purge tank 640 and water may be stored near the bottom of purge tank 640. As water flows into purge tank 640 the level of the water may rise from the bottom toward the top of purge tank 640. Fuel from the top of purge tank 640 (e.g., above lateral plane 645) is purged out of purge tank 640 to the fuel tank 610 via purge line 634. Further, a check valve 630 is positioned at the top of purge tank 640 in purge line 634. While check valve 630 is illustrated as being positioned outside of purge tank 640, in some embodiments check valve 630 may be positioned inside of purge tank 640. Check valve 630 is adapted to allow a flow of fuel from purge tank 640 to fuel tank 610 while blocking a flow of fuel from fuel tank 610 to purge tank 640.

Check valve 630 may prevent air from entering the fuel system. For example, the check valve 630 may have a set pressure point that is high enough to prevent air from purge tank 640 from being sucked into fuel tank 610 when pump 250 is operating. When purge tank 640 is filled with fuel, water, and/or a fuel-mix from fuel-water separator 220, the pressure in purge tank 640 may increase above the set pressure point of check valve 630 to allow the fuel in purge tank 630 to be purged back to the fuel tank 610. Further, check valve 630 prevents draining of fuel from fuel tank 610 and/or purge line 634 back to the purge tank 640. Such drain-back may cause hard starting of the engine and/or lead to multiple priming attempts before the engine may be started. By including check valve 630, priming time may be decreased and fuel drain-back may be prevented once the system is initially primed.

An interior volume of purge tank 240 may be large enough for locomotive 100 to operate for an extended period without purge tank 640 filling with water. In one embodiment, the volume of purge tank 640 may be greater than or equal to the volume of water to be extracted from fuel when locomotive 100 is operated under typical or worst-case conditions between scheduled maintenance periods, such as a period of 180 days. For example, the volume of purge tank 640 may be sized according to average fuel consumption (e.g. miles per gallon) of locomotive 100, an average distance to be travelled by locomotive 100, and an average water content of fuel. In another example, the volume of purge tank 640 may be sized according to worst-case fuel consumption of locomotive 100, a worst-case distance to be travelled, and a worst-case water content of fuel. In this manner, purge tank 640 may not fill up with water between scheduled maintenance periods of locomotive 100. However, some conditions may lead to purge tank 640 filling with water before the maintenance period. For example, out of specification fuel (e.g. fuel with a water concentration in excess of the specified amount), water leaking into fuel system 605, and increased fuel consumption (e.g. burning more fuel and extracting more water) may result in purge tank 640 filling more quickly than expected.

Once purge tank 640 is filled with water, water may be drained out of purge tank 640 via a drain 642 positioned at the bottom of purge tank 640. Drain 642 may be a manually-operated drain that, when opened, evacuates water out of purge tank 640 via gravity and/or fuel pressure. Water may be drained from purge tank 640 responsive to an indication the water level has reached a threshold level, as explained below, during scheduled routine maintenance, or during other conditions.

One or more fuel property sensors may be included in fuel system 605 to detect the amount of water in the fuel in fuel tank 610 and/or purge tank 640, and/or to determine parameters of the fuel provided to the engine 106. For example, sensor 680 may be positioned near the top of purge tank 640 and optional sensor 681 may be positioned in fuel tank 610. Sensors 680 and 681 may determine the amount of free and dissolved water in fuel, thus allowing detection of variable water levels rather than simple yes/no water detection provided by sensors 270 and/or 280 of FIG. 2, for example.

Sensors 680 and 681 may each include multiple sensing elements, including a first element for measuring kinematic viscosity, a second element for measuring dielectric constant, and a third element for measuring temperature of the fluid (e.g., fuel, water, or fuel-water mixture) contacting the respective sensor elements. In one embodiment, the three sensing elements are contained within a common sensor housing. Based on the kinematic viscosity, dielectric constant, and optionally further based on temperature, the amount of water in the fuel may be determined. For example, the amount of water in the liquid contact the sensor may be determined based on the measured dielectric constant, and in some examples also based on the kinematic viscosity. Further, properties of the fuel may be determined (e.g., density) based on the kinematic viscosity, dielectric constant, and temperature of the fuel measured by the fuel property sensor and used in fuel energy calculations to optimize engine operating parameter settings, such as power output and emissions via adjusting of fuel injection amounts, fuel injection timings, etc., based on the fuel energy calculations.

In some examples, fuel system 605 may include both sensors 680 and 681. Sensor 680 may be used to detect the presence of water at the top of the purge tank 640. For example, as illustrated in FIG. 6, sensor 680 may be positioned at the lateral plane 645 of the purge tank. If water is detected (or an amount of water above a threshold) by the sensor 680, it may indicate that the amount of water in purge tank 640 is above a desired threshold (e.g., when water is detected at the level of the sensor, it may indicate that water exceeds a threshold level in the purge tank). Accordingly, a visual display notification may be provided to an operator of locomotive 100 to drain purge tank 640. Further, fuel parameters of the fuel provided to the engine may be approximated based on the fuel parameters of the fuel being purged from purge tank 640 to fuel tank 610 as detected by sensor 680. The amount of water in the fuel, fuel quality, fuel density, and/or other parameters of the fuel in the purge tank that is purged to the fuel tank may be determined. The fuel parameters measured by the sensor 680 in the purge tank 640 may be used to estimate the same fuel parameters of the fuel in the fuel tank by taking into account the flow rate of the fuel into the fuel tank and/or the ratio of the volume of fuel in the purge tank to the volume of fuel in the fuel tank.

When included, sensor 681 may be used to determine the parameters of the fuel provided to the engine for the fuel energy calculations discussed above. Further, sensor 681 may be used to determine the amount of water mixed with fuel in the fuel tank 610. If the amount of water is above a threshold, the concentration of water mixed with fuel from fuel tank 610 may exceed the concentration of water that may be separated by fuel-water separator 220 when fuel is pumped near a peak flow rate. Thus, if a threshold amount of water is detected, fuel may be pumped at a reduced rate of flow to enable fuel-water separator 220 to separate the water and to deliver dry fuel to engine 106.

In other examples, fuel system 605 may only include sensor 680 or only include sensor 681. In examples where only sensor 681 is present and sensor 680 is dispensed with, purge tank 640 may be drained at scheduled times, or the water level in purge tank 640 may be estimated based on the water concentration of fuel in fuel tank 610 and the flow rate of fuel across fuel-water separator 220.

Thus, fuel system 605 includes a fuel tank 610 housing fuel to be combusted in engine 106. The fuel in fuel tank 610 may include water in some conditions. Water in the fuel may be separated by fuel-water separator 220. The dry fuel from fuel-water separator 220 may be provided for combustion in the engine 106, while the water and/or fuel-water mix from fuel-water separator 220 may be drained to purge tank 640 via duct 632. Purge tank 640 may be separate from fuel tank 610. Fuel included in the fuel-water mix drained to purge tank 640 may be less dense than water and thus rise to the top of purge tank 640 and eventually be purged back to fuel tank 610 via purge line 634 (which is in fluid communication with purge tank 640 and fuel tank 610) and check valve 630. Water in the purge tank 640 may be drained out of the purge tank via drain 642. As such, a fuel polisher may be dispensed with. However, in some embodiments water drained from purge tank 640 via drain 642 may be processed and any fuel recovered provided back to fuel tank 610. Various properties of the fuel, including water concentration, may be determined by one or more of sensors 680 and 681. Sensors 680 and 681 may measure the kinematic viscosity, dielectric constant, and temperature of the fluid in the purge tank 640 and/or fuel tank 610. The fuel properties may be utilized by the controller to adjust fueling parameters, such as fuel flow rate, fuel injection amount, fuel injection timing, ignition timing, etc., to provide a desired power output, emissions, etc.

As explained previously with respect to FIGS. 2 and 4-5, fuel-water separator 220 may include a sensor 270 to detect water in fuel-water separator 220, and if water is detected by sensor 270, the engine may be shutdown or the rate of fuel flow may be decreased to prevent water being supplied to the engine. Fuel system 605 similarly includes sensor 270 and controller 110, and is also configured to shutdown the engine or decrease the rate of fuel flow to prevent water being supplied to the engine when sensor 270 detects water.

Thus, FIG. 6 provides for a water drainage system for a fuel system, the water drainage system comprising: a fuel tank; a fuel-water separator in fluid communication with the fuel tank; a purge tank in fluid communication with the fuel-water separator and the fuel tank, the purge tank separate from the fuel tank; a fuel property sensor for detecting a presence of water; and a purge line in fluid communication with the purge tank for removing fluid from the purge tank, a flow of the fluid from the purge tank controlled by a check valve.

The fuel property sensor may comprise a first element to measure kinematic viscosity, a second element to measure dielectric constant, and a third element to measure temperature. In some examples, the fuel property sensor may comprise multiple outputs, each output configured to transmit a respective one of the measured kinematic viscosity, dielectric constant, and temperature to a controller.

In one example, the fuel property sensor is operably coupled to the purge tank. In another example, the fuel property sensor is operably coupled to the fuel tank. The check valve may be positioned in the purge line near a top of the purge tank, and the purge tank may include a drain for draining water out of the purge tank. The water drainage system may further comprise a separator water sensor operably disposed in the fuel-water separator for detecting a presence of water.

Another embodiment relates to a vehicle system, comprising: a fuel tank; a fuel-water separator in fluid communication with the fuel tank; a separator water sensor operably disposed in the fuel-water separator for detecting a presence of water; an engine in fluid communication with the fuel-water separator; a duct in fluid communication with the fuel-water separator; a purge tank in fluid communication with the duct and the fuel tank, the purge tank receiving liquid from the duct via an outlet near a bottom of the purge tank, the purge tank separate from the fuel tank; a fuel property sensor operably disposed in the purge tank for detecting a presence of water; a purge line in fluid communication with the purge tank and the fuel tank for removing fluid from the purge tank; a fuel drain-back prevention valve in the purge line; and a controller in communication with the separator water sensor, the fuel property sensor, and the engine and configured to: detect if a water level exceeds a threshold level in the purge tank; and detect if a water level exceeds a threshold level in the fuel-water separator.

The controller may be further configured to output a notification to an operator of the vehicle system if the water level exceeds the threshold level in the purge tank. The controller may be further configured to stop the engine in response to a water level exceeding the threshold level in the fuel-water separator.

The fuel property sensor may measure kinematic viscosity, dielectric constant, and temperature and determine the presence of water in the purge tank at the sensor based on one or more of the kinematic viscosity, dielectric constant, and temperature. The controller may be further configured to adjust one or more engine fueling parameters based on the measured kinematic viscosity, dielectric constant, and temperature.

Turning now to FIG. 7, a method 700 for operating a vehicle, such as locomotive 100, including a fuel system, such as fuel system 605, is presented. Method 700 may be carried out according to non-transitory instructions stored in a memory of a controller, such as memory 202 of controller 110, in order to manage water in the fuel system 605 of FIG. 6.

At 710, a first mixture of fuel and water may be pumped from a fuel tank. For example, pump 250 may pump fuel entrained with water from fuel tank 210. In one embodiment, the fuel and water may be heated with a heater, such as heater 252. At 720, the first mixture of fuel and water may be separated into fuel and a second mixture of fuel and water. For example, fuel-water separator 220 may separate the fuel entrained with water into dry fuel and purge liquid. The purge liquid may include a second mixture of fuel and water, where the water is less emulsified in the fuel.

At 730, the separated dry fuel may be delivered to the engine. For example, dry fuel may flow from fuel-water separator 220 through fuel pressure regulating valve 260 to engine 106. Fuel pressure regulating valve 260 may limit the fuel pressure of the dry fuel to less than a peak fuel pressure of engine 106.

At 740, the second mixture of fuel and water may be delivered to a purge tank separate from the fuel tank. For example, the purge liquid may be delivered to purge tank 640 via an outlet of duct 632 near the bottom of purge tank 640.

At 750, fuel may be returned from the purge tank to the fuel tank. For example, water, having a greater density than fuel, may remain near the bottom of purge tank 640 and fuel may rise to near the top of purge tank 640. When purge tank 640 is full of water and fuel, and when purge liquid enters purge tank 640 through duct 632, fuel may flow through a purge line 634 back to fuel tank 210. The fuel may flow through purge line 634 via a fuel drain-back prevention valve (e.g., check valve 630) that allows flow of fuel from the purge tank to the fuel tank but prevents flow of fuel from fuel tank to purge tank.

At 760, a sensor coupled to the purge tank may indicate if water exceeds a threshold level in the purge tank. For example, a fuel property sensor 680 may be coupled to purge tank and output from the sensor 680 may indicate to controller 110 when water reaches the level of purge tank water sensor 280. During typical operation of locomotive 100, water may remain below the threshold level of purge tank

640. However, out-of-specification fuel having too much water, water leaks into fuel system 605, increased fuel consumption of locomotive 100, or delayed maintenance may lead to water in purge tank 640 exceeding a threshold level. If water is detected at the level of the sensor 680, it may be determined water in the purge tank exceeds the threshold level, and a first notification may be output, for example, to an operator of the locomotive to drain the purge tank 640.

The presence and/or amount of water may be detected based on a dielectric constant measured by the sensor 680, as indicated at 762. For example, the dielectric constant of water is substantially higher than diesel fuel or air (e.g., water may have a dielectric constant near 80, while diesel may have a dielectric constant near 2 and air may have a dielectric constant near 1), and thus the amount of water in the fluid (e.g., water, fuel, water-fuel mixture, air) at the level of the sensor in the purge tank may be determined based on the measured dielectric constant.

Alternatively or additionally, in some examples, the presence and/or amount of water may be detected based on a kinematic viscosity measured by the sensor 680, as indicated at 764. For example, the kinematic viscosity of diesel fuel may be higher than the kinematic viscosity of water, and thus the amount of water in the fluid (e.g., water, fuel, water-fuel mixture, air) at the level of the sensor in the purge tank may be determined based on the measured kinematic viscosity. However, because the kinematic viscosity of diesel fuel may vary based on the composition of the fuel, and in some examples may be near the viscosity of water, the kinematic viscosity may utilized as a back-up or rationality check for the water determination based on the dielectric constant. Further, the kinematic viscosity may be used to determine the amount of water in the purge tank only if the composition of the fuel is known. Further still, the kinematic viscosity of the liquid measured by the sensor is temperature-dependent, and thus the temperature may also be measured by the sensor to determine the amount of water in the purge tank.

At 770, one or more engine operating parameters may be adjusted based on one or more properties of the fuel in fuel tank 610, as measured by the sensor 680. As explained above, fuel property sensor 680 may measure the kinematic viscosity, dielectric constant, and temperature of the liquid in the purge tank 640. During most operating conditions, the liquid contacting sensor 680 may be comprised of fuel or a fuel-water mixture that is subsequently purged back to fuel tank 610. Thus, the sensor 680 may measure the kinematic viscosity, dielectric constant, and temperature of the fuel that is returned to the fuel tank. As indicated at 772, these three parameters of the fuel measured by the sensor may be used to determine various properties of the fuel, including fuel quality (e.g., octane level, level of fuel contaminants, etc.), fuel water content, fuel density, etc. Based on the determined fuel properties, one or more engine operating parameters may be adjusted to maintain desired engine output and/or emissions. For example, the fuel injection amount and/or timing, notch throttle setting, engine speed, exhaust gas recirculation amount, boost pressure, etc., may be adjusted based on the determined fuel parameters.

Additionally, as indicated at 774, the fuel properties of the fuel in the fuel tank 610 may be further based on the fuel flow rate and/or volume ratio between the purge tank and the fuel tank. As explained above, fuel property sensor 680 may measure the parameters of the fuel in the purge tank and not in the fuel tank. Thus, the properties of the fuel in the fuel tank may be estimated based on the measured parameters of the fuel in the purge tank. The estimation may take into account the flow rate of fuel from the purge tank to the fuel tank and/or the ratio of the volume of the fuel in the purge tank to the volume of fuel in the fuel tank. However, in some embodiments fuel tank 610 may be operably coupled to its own fuel property sensor (e.g., sensor 681) and thus the properties of the fuel in the fuel tank 610 may be measured directly. In still further embodiments, the amount of water in the fuel in fuel tank 610 may be estimated based on the output from the sensor coupled to the fuel-water separator 220 and the fuel flow rate across the fuel-water separator.

By utilizing a fuel property sensor to both detect the presence of water in the purge tank and determine the properties of the fuel for engine operating adjustments, additional sensors that might otherwise be needed may be dispensed with. Further, by using a fuel property sensor that measures kinematic viscosity, dielectric constant, and temperature a redundant sensor is provided, allowing for more accurate measurements of the water content and other fuel parameters. For example, a rationality check may be provided by comparing the properties of the fuel (e.g., fuel composition) as measured by the dielectric constant to the properties of the fuel as measured by the kinematic viscosity and/or temperature. If a discrepancy in the measurements is detected, a diagnostic routine may be initiated to determine if one more elements of the sensor is degraded.

At 780, a sensor operably disposed in the fuel-water separator may indicate if water exceeds a threshold level in a fuel-water separator. For example, separator water sensor 270 may indicate to controller 110 when water exceeds the threshold level in fuel-water separator 220. In one example, water may be detected if the concentration of water in fuel being pumped from fuel tank 610 exceeds the capacity of water to be separated in fuel-water separator 220. For example, the rate of water flowing into fuel-water separator 220 may exceed the rate of purge liquid flowing from fuel-water separator 220 to purge tank 640. In one example, duct 632 may be clogged and the flow of purge liquid may be reduced.

At 790, the engine may be stopped if water exceeds the threshold level in the fuel-water separator. For example, separator water sensor 270 may indicate to controller 110 that water exceeds the threshold level in fuel-water separator 220, and controller 110 may stop engine 106 in response thereto. Thus, engine 106 may be protected from undesirable effects of combusting fuel mixed with water. In other examples, the flow rate of fuel pumped from the fuel tank 610 to the fuel-water separator 220 may be reduced in response to water exceeding the threshold level in the fuel-water separator, as explained above with respect to FIG. 5.

Thus, method 700 of FIG. 7 provides for A method of operating a vehicle comprising pumping a first mixture of fuel and water from a fuel tank; separating the first mixture of fuel and water into separated fuel and a second mixture of fuel and water; delivering the separated fuel to an engine of the vehicle; delivering the second mixture of fuel and water to a purge tank separate from the fuel tank; returning fuel from the purge tank to the fuel tank; and outputting a first notification if water exceeds a threshold level in the purge tank.

The method may include wherein returning fuel from the purge tank to the fuel tank comprises returning the fuel from the purge tank to the fuel tank via a check valve positioned in a purge line fluidically coupling the purge tank to the fuel tank, the check valve preventing drain-back of fuel from the fuel tank to the purge tank.

The method may also comprise wherein outputting the first notification if water exceeds the threshold level in the purge tank comprises determining if water exceeds the threshold level in the purge tank via a sensor coupled to the purge tank, and outputting the first notification if the water exceeds the threshold level. Determining if water exceeds the threshold level in the purge tank via the sensor coupled to the purge tank may comprise detecting a presence of water in the purge tank at the sensor based on a dielectric constant measured by the sensor. The presence of water in the purge tank may be further detected based on a kinematic viscosity measured by the sensor.

In some examples, outputting the first notification if water exceeds the threshold level in the purge tank comprises estimating if water exceeds the threshold level in the purge tank based on a water concentration of fuel in the fuel tank determined by a sensor coupled to the fuel tank and a flow rate of fuel, and outputting the first notification if the water exceeds the threshold level.

The method may further comprise determining one or more parameters of fuel in the fuel tank based on a kinematic viscosity, dielectric constant, and temperature of fuel in the purge tank measured by the sensor, and further based on a flow rate of fuel from the purge tank to the fuel tank. The method may further comprise adjusting one or more engine operating parameters based on the determined one or more parameters of the fuel in the fuel tank.

The method may include indicating if a water level exceeds a threshold level in a fuel-water separator via a sensor operably disposed in the fuel-water separator; stopping the engine in response to the water level exceeding the threshold level in the fuel-water separator; and outputting a second notification in response to the sensor operably disposed in the fuel-water separator indicating the water level exceeds the threshold level in the fuel-water separator.

An example method may include sensing, through first, second, and third distinct sensing elements of a sensor coupled to a collected of a water/fuel separator, each of viscosity, dielectric constant, and temperature, where engine operation is stopped in response to a water amount sensed greater than a threshold via one or more of the viscosity and dielectric constant; and otherwise continuing engine operation, where the engine fuel injection and engine speed are adjusted responsive to a fuel quality and temperature, the fuel quality being sensed variably through a range based on one or both of the viscosity and dielectric constant. The variable range is more than a presence or absence of water in fuel, but rather may be proportional to both a water concentration sensed as well as other fuel quality indicative parameter that may be based on viscosity, temperature, and the sensed dielectric constant.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims. Moreover, unless specifically stated otherwise, any use of the terms first, second, etc., do not denote any order or importance, but rather the terms first, second, etc., are used to distinguish one element from another.

The invention claimed is:

1. A vehicle system, comprising:
a fuel tank;
a fuel-water separator in fluid communication with the fuel tank;
a separator water sensor operably disposed in the fuel-water separator for detecting a presence of water in the fuel-water separator;
an engine in fluid communication with the fuel-water separator;
a purge tank in fluid communication with the fuel tank;
a duct coupled between the fuel-water separator and the purge tank, the purge tank receiving liquid from the duct via an outlet at a bottom of the purge tank, the purge tank separate from the fuel tank;
a fuel property sensor operably disposed in the purge tank for detecting a presence of water at a top of the purge tank;
a purge line in fluid communication with the purge tank and the fuel tank for removing fuel from the purge tank;
a fuel drain-back prevention valve in the purge line; and
a controller in communication with the separator water sensor, the fuel property sensor, and the engine and configured to:
  detect if a water level exceeds a threshold level in the purge tank; and
  detect if a water level exceeds a threshold level in the fuel-water separator; and
wherein the fuel removed from the purge tank via the purge line is supplied to the fuel tank, the fuel property sensor operably disposed in the purge tank is a first fuel property sensor, and further comprising a second fuel property sensor operably disposed in the fuel tank and configured to detect a concentration of water mixed with the fuel in the fuel tank.

2. The vehicle system of claim 1, wherein the controller is further configured to output a notification to an operator of the vehicle system if the water level exceeds the threshold level in the purge tank.

3. The vehicle system of claim 1, wherein the controller is further configured to stop the engine in response to the water level exceeding the threshold level in the fuel-water separator.

4. The vehicle system of claim 1, wherein the fuel property sensor measures kinematic viscosity, dielectric constant, and temperature and determines the presence of water in the purge tank at the fuel property sensor based on one or more of the kinematic viscosity, dielectric constant, and temperature.

5. The vehicle system of claim 4, wherein the controller is further configured to adjust one or more engine fueling parameters based on the measured kinematic viscosity, dielectric constant, and temperature.

6. The vehicle system of claim 1, wherein the controller is configured to:
output a notification to an operator of the vehicle system responsive to feedback from the first fuel property sensor inducing a level of water in the purge tank exceeds a first threshold level;
adjust one or more engine operating parameters based on output from the second fuel property sensor; and
stop the engine responsive to feedback from the separator water sensor indicating a level of water in the fuel-water separator exceeds a second threshold level.

7. The vehicle system of claim 6, wherein one or more engine operating parameters comprise one or more of fuel flow rate, fuel injection amount, fuel injection timing, throttle setting, and engine speed.

* * * * *